United States Patent [19]

Skole et al.

[11] 3,950,225

[45] Apr. 13, 1976

[54] MEDIUM, COMPONENT THEREOF AND PROCESS EMPLOYING SAME FOR THE PRODUCTION OF MICROBIAL INSECTICIDES, SUCH AS *BACILLUS POPILLIAE* SPORES AND THE LIKE, FOR THE CONTROL OF JAPANESE BEETLES AND OTHER INSECTS

[75] Inventors: Richard David Skole, Elmhurst, N.Y.; Anthony Benny Rizzuto, Piscataway, N.J.

[73] Assignee: Amstar Corporation, New York, N.Y.

[22] Filed: Oct. 15, 1974

[21] Appl. No.: 514,473

[52] U.S. Cl. ................................. 195/96; 195/100
[51] Int. Cl.$^2$ .......................................... C12K 1/10
[58] Field of Search ................ 195/11, 96, 99–103; 426/257, 489

[56] References Cited
UNITED STATES PATENTS 3,087,865 4/1963 Drake et al. .......................... 195/96

OTHER PUBLICATIONS

W. E. Haynes et al., "Spore Formation by *Bacillus popilliae* in Liquid Medium Containing Activated Carbon" J. of Bact. 91, pp. 2270–2274 (1966).

*Primary Examiner*—A. Louis Monacell
*Assistant Examiner*—C. A. Fan
*Attorney, Agent, or Firm*—Cooper, Dunham, Clark, Griffin & Moran

[57] ABSTRACT

Char waste water, a waste product in sugar refining, derived by water washing spent animal charcoal (char), is useful as a sporulation medium for the production of *Bacillus popilliae* spores. *Bacillus popilliae* spores are useful as a microbial insecticide in the control of Japanese beetles since *B. popilliae* spores cause milky disease in the Japanese beetle and other insects, such as the European chafer.

10 Claims, No Drawings

MEDIUM, COMPONENT THEREOF AND PROCESS EMPLOYING SAME FOR THE PRODUCTION OF MICROBIAL INSECTICIDES, SUCH AS BACILLUS POPILLIAE SPORES AND THE LIKE, FOR THE CONTROL OF JAPANESE BEETLES AND OTHER INSECTS

This invention is related to microbial pesticides or insecticides. In one embodiment, this invention is directed to a component of a medium useful for the sporulation of the vegetative cells of certain microorganisms, such as Bacillus popilliae. In another embodiment, this invention is directed to the preparation of a medium useful for the sporulation of the vegetative cells of B. popilliae and like microorganisms. In still another embodiment, this invention is directed to a method for the production of spores of B. popilliae and similar bacterial spores.

Microbial or bacterial pesticides or insecticides are known and are produced and employed commercially in the United States. One of the best known bacterial insecticides is based on the bacterium Bacillus thuringiensis. This microorganism is the causative agent of fatal disease in many lepidopterous (caterpillar) insects, e.g., cabbage looper, alfalfa caterpillar, the so-called imported cabbage worm, tent caterpillar and gypsy moth. This microorganism, B. thuringiensis, is easily cultivated in various media and spores and the spores thereof can be mass-produced by conventional fermentation techniques.

Another microbial insecticide is based on the microorganism B. popilliae which causes milky disease of the Japanese beetle and the European chafer. In the production of this microbial insecticide, the spores of B. popilliae, living insect larva, such as the grub of the Japanese beetle, are injected with the pathogen, i.e., the spores of B. popilliae. After a short incubation period, the injected larvae containing the spores of B. popilliae are ground and mixed with an extending material, such as talc.

The above-described process for the production of the spores of B. popilliae is a difficult, costly process, for more details see U.S. Pat. No. 2,293,890. Various techniques have been disclosed for improving the production, collection and utilization of the spores of B. popilliae as a microbial insecticide, see U.S. Pat. Nos. 3,308,038, 3,503,851 and 3,616,250. The disclosures of the above-identified patents are herein incorporated and made part of this disclosure.

It is an object of the invention to provide a component useful in the make-up of a substrate or medium for the sporulation of vegetative cells of the microorganism B. popilliae.

It is another object of this invention to provide a medium useful for effecting sporulation of vegetative cells of B. popilliae.

It is another object of this invention to provide a process for effecting the sporulation of microorganisms, particularly bacteria, which undergo sporulation.

How these and other objects of this invention are achieved will become apparent in the light of the accompanying disclosure. In at least one embodiment of the practices of this invention, at least one of the foregoing objects will be achieved.

It has been discovered that char waste water is useful as a component of a medium for the sporulation of spore-producing microorganisms, such as B. popilliae.

Char waste water is a waste product of sugar refining, such as cane sugar refining. In the refining of cane sugar, animal charcoal (char), such as bone char, which is the granular residue obtained by the destructive distillation, is employed. In the processing of sugar liquors or syrups, after clarification by defecation, the remaining color bodies and other impurities in the sugar syrups or liquors must be removed before a satisfactory refined crystallized sugar is produced. These color bodies and other impurities are removed from the defecated, filtered sugar syrups and liquors by percolation and filtration of the sugar syrups and liquors through cisterns or tanks filled with animal charcoal (char). After the ability of the char to remove color and other impurities from the sugar syrups and liquors undergoing treatment by contact with the char, the char cisterns or filters are "sweetened off" or washed with hot water. After about 12 to 14 hours washing, the sugar content of the resulting wash water is no longer sufficient to warrant recovery of the sweet or sugar-containing wash water for the eventual recovery of sugar therefrom. At that time, the wash water is usually turned to waste, the washing of the char to waste continuing for about 12–24 hours, more or less, usually about 14–18 hours. During this period of washing the char to waste, there is produced the char waste water useful in the practices of this invention. Analyses of typical char waste waters and ranges for the components thereof are set forth in accompanying Table I.

TABLE I

| Component | Analyses of Char Waste Water Range % By Wt. | Char Waste Water A — % By Wt. | Char Waste Water B — % By Wt. |
| --- | --- | --- | --- |
| Sucrose | 0.3–2.5 | 0.60% | 1.58% |
| Reducing Sugars | 0.03–0.15 | 0.054% | 0.082% |
| Ash Sulfated | 0.3–0.8 | 0.40% | 0.45% |
| Ash Thermal | 0.15–0.4 | 0.255% | 0.256% |
| Solids (Drying) | 1.1–2.1 | 1.30% | 1.58% |
| ppm Calcium | 500–1500 | 792 | 850 |
| ppm Magnesium | 60–150 | 93.8 | 105 |
| ppm Sodium | 20–90 | 32.5 | 64 |
| ppm Potassium | 50–500 | 117 | 247 |
| ppm Iron | 0.2–9.0 | 1.3 | 3.92 |
| ppm Copper | 0.4–0.9 | 0.61 | 0.57 |
| ppm Zinc | 0.05–0.3 | 0.18 | 0.12 |
| ppm Manganese | 0.1–0.8 | 0.33 | 0.29 |
| ppm Sulfates | 100–1200 | 282 | 689 |
| ppm Phosphates | 6–40 | 15.96 | 13 |
| ppm Chlorides | 1–60 | 2.1 | 13.2 |

As indicated hereinabove, bone char is employed in sugar refinery operations to remove color bodies and other impurities from sugar syrups just prior to crystallization of sugar therefrom. Bone char is usually made by heating degreased, crushed and grated animal bones in a close retort (in the absence of air) to a cherry red heat until most of the organic matter has been destroyed, volatilized or driven off. The structure of the bone char consists of a porous framework of calcium phosphate coated with carbon and is composed structurally of calcium phosphate and some calcium carbonate. The carbon content is made up of substantially elemental carbon and chemically combined carbon. A percent by weight chemical analysis of bone char is substantially as follows: carbon 8.5–10, insolubilized ash 0.2, sulfate (as $CaSO_4$) 0.08, sulfide (as CaS) 0.07, carbonate (as $CaCO_3$) 7.9, iron 0.07, phosphate (as $CaPO_4$) 80.6–84.1.

In the washing to spent bone char after the sweetening off operation which is primarily carried out to displace the sugar-containing liquor from the char cisterns or filters, the bone char having completed its primary function of absorbing selected impurities into its high porous structure, and when the amount of dissolved sugar in the sweet-water washing reaches a low level or concentration which does not justify the recovery of sugar therefrom, the washing operation is continued for an extended period of time up to about 24 hours, more or less, with relatively hot water, such as water having a temperature in the range from about 130°–200°F., to remove the adsorbed impurities, primarily ash (salts) and loosely absorbed color bodies. Upon completion of the water washing operation with the production of char waste water, the resulting washed bone char is then burned in the kiln to remove any residual impurities and to regenerate the bone char.

The analyses of typical char waste waters of Table I show a very low level of carbohydrates (primarily sucrose and invert sugar). The analyses, however, show a wide range of inorganic ions which are indispensible for the sporulation of various Bacillus species. It is known that inorganic ions are essential for the formation of bacterial spores and the level or concentration of the inorganic ions required for sporulation varies with the microorganism, the concentration of nutrients, oxygen supply, temperature and pH. The specific function of minerals or inorganics in sporulation, however, is unknown. It has been speculated that inorganic ions act as catalysts in the activation of the many enzyme systems involved in sporulation.

Of the metals or inorganic ions, manganese has been shown to be required for sporulation, see the article by J. Charney et al. entitled "Manganese as an Essential Element for Sporulation in the Genus Bacillus," appearing in J. Bact. 62, 145–148 (1951). Calcium also is required for the formation of resistant spores and is necessary at the time of sporangium formation. Calcium is also known to be required for thermoresistance and in this capacity is closely associated with dipicolinic (DPA), see the article by H. O. Halvorson et al. entitled "The Role of DPA in Bacterial Spores II," 149–164 (1961) published by Burgess Publishing Co., Minneapolis, Minn. Copper has been associated with various enzymatic reactions as a co-factor or as a metal ion activator and the need for iron and zinc for sporulation has been reported, see the article by H. R. Curran et al. entitled "The Influence of Iron or Manganese Upon the Formation of Spores by Mesophilic Aerobes in Fluid Organic Media," appearing in J. Bact. 67, 489–497 (1954). It has also been reported producing a medium deficiency in potassium, phosphates and comprises prevents most Bacillus from sporulating or reduces the number of spores reduced, see the article by J. W. Foster et al. entitled "Mineral Deficiencies in Complex Organic Media as Limiting Factors in the Sporulation of Aerobic Bacilli," appearing in J. Bact. 57, 613–615 (1949).

The relationship of charcoal and increased sporulation was noted by J. L. Roberts et al in the article entitled "Spore Formation by *Bacillus subtilis* in Peptone Solution Altered by Treatment with Activated Charcoal," appearing in J. Bact. 44, 653–659 (1942); also, the article by J. W. Foster et al entitled "Antisporulation Factors in Complex Organic Media. I. Growth and Sporulation on Bacillus larvae," appearing in J. Bact. 59, 463–470 (1950), reported an increase in the sporulation percent of *B. larvae* by treating several bacteriological media with activated charcoal. These investigators noted that charcoal treatment was conceivably more effective in enhancing sporulation than it was in increasing vegetative growth. K. H. Steinkrous et al. in their paper entitled "Studies on the Milky Disease Organisms," Journal Paper No. 1086, New York State Agricultural Experimental Station, Geneva, N.Y., reported that when activated charcoal was added to a solid triptone agar medium, spores of *B. popilliae* could be produced and W. C. Haynes et al. reported in their article entitled "Spore Formation by *Bacillus popilliae* in Liquid Medium Containing Activated Carbon," appearing in J. Bact. 91, 2270–2274 (1966), the successful sporulation of *B. popilliae* in a liquid medium containing activated carbon; however, low spore yields, about 3%, were reported. Also, W. C. Haynes et al. in their article entitled "Hydrolyzed Casein Enhances the Sporogenicity of Yeast Products for *Bacillus popilliae* in Liquid Cultures," Abstracts of Annual Meeting, G145 American Society for Microbiology (1973), reported that *B. popilliae* NRRLB 2309S formed as many as 3.1 $\times 10^7$ refractile of resistant spores/ml in a liquid shaken culture containing glucose, $K_2HPO_4$, activated carbon, yeast and casein hydrolysate. In none of the above-identified publications, the disclosures of which are herein incorporated and made part of this disclosure, is there any teaching or suggestion of the utility of char waste water, such as described above and/or produced in a cane sugar refining operation, as a component of a sporulation medium, particularly for the sporulation of B. popilliae.

The following is exemplary of the practices of this invention. Bacillus popilliae NRRLB-2309, in the form of a 4% inoculant of 72 hour frozen spore cultures, was inoculated into three 25 ml portions of a medium for the vegetative growth of *B. popilliae*. The medium for vegetative growth comprised 1.5% yeast extract, 0.3% $K_2HPO_4$, 0.2% glucose and 0.5% triptose, the pH of the medium having been adjusted to 7.2–7.3 and sterilized for 15 minutes at 120°C. The inoculated flasks were incubated on a rotary shaker at 200 rev/min at 27°C. for 24 hours. The resulting cultured vegetative cells were centrifuged and washed three times to remove all traces of the vegetative growth medium. 6.5 ± 0.5 grams of the washed vegetative cells of *B. popilliae* were then employed to inoculate 5 liters of sterile filtered char waste water, the char waste water having first been filtered through glass wool, the pH adjusted to 7.0 and sterilized for 40 minutes at 121°C. The fermentation of the inoculated char waste water was carried out in a 14 liter New Brunswick Scientific Co. Micro Ferm laboratory fermentor. The controls of the fermentator were set for the introduction of 0.2 vol per vol per minute of sterile air, the agitator set for 200 rpm and the temperature maintained at 25°C. with no pH control. The inoculated char waste water was incubated for a period of 72 hours.

Viable (vegetative) and spore counts were made at 24 hours intervals and the spores were heated at 75°C. for 15 minutes. The above-described vegetative growth medium solidified with 2% agar was used for both viable and spore counts by the membrane filtration method. Microscopic stains were made to determine spore characteristics and DPA determinations were made of the harvested spores. The spores were harvested by the addition of 50 grams of talc, U.S.P., to the 5 liters of the inoculated char waste water after the 72 hour inoculation period. The incubated talc-containing char waste water was then centrifuged and the talc-spore mixture recovered and dried for 24 hours at 45°C. at subatmospheric pressure.

In the practice of this invention, the char waste water need not be a composite of the total char waste water. It has been found that the char waste water collected at various times during the water washing operation producing the resulting char waste water produced char waste water satisfactory for use in a sporulation medium in accordance with this invention. Indeed, the char waste water samples collected during portions of the washing operation or samples of the total char waste water all yielded 100 percent sporulation.

The two-stage fermentation procedure described hereinabove employing cane sugar refinery char waste water as a sporulation medium greatly exceeded the sporulation rates of the various reported charcoal media as indicated in accompanying Table II.

TABLE II

| Reported Sporulation Rates of Charcoal-Containing Media | |
|---|---|
| Charcoal Media | Percent Sporulation |
| J Medium — 10% Charcoal * | 18.8% |
| J Medium — 10% Charcoal * | 8.6% |
| MYPT Medium — 10% Charcoal ** | 0.13% |
| S-P Medium — 3% Charcoal *** | 7.5% |
| S-P Medium — 3% Charcoal *** | 13.6% |

* Sporulation of *Bacillus popilliae* in liquid medium as affected by kind of carbon and method of sterilization. Haynes, W. C., Weih, L. J., Crowell, C. Can. J. Microbiol. 18:515–518 (1971)

** Characteristics of a new strain of *Bacillus popilliae* sporogenic in vitro. Sharpe, E. S., St. Julian, G., Crowell, L. Applied Microbiology 681–688 (1970)

*** Studies on the Milky Disease Organisms. Steinkrous, K. H., Provvidenti, M. J. Journal Paper No. 1086 New York State Agricultural Exp. Station Geneva, New York Further, the practices of this invention provide an effective means for producing large numbers of *B. popilliae* spores without using complex media, prolonged incubation periods and/or other techniques not readily suitable for large-scale fermentation production.

Although the practices of this invention have been indicated to be applicable to the production of spores of *Bacillus popilliae*, this invention is generally applicable to the production of microorganisms, particularly bacterial spores. Other spores which are suitably produced in accordance with the practices of this invention include the spores of *Bacillus lentimorbus* which also produce the milky disease in larval stages of insects. Those bacteria which form spores, particularly endospores, are usefully employed in the practices of this invention. Those bacteria which form endospores appear to be limited to a small group of eubacteria family *Bacillaceae*, and *Vibrio spirilla* and sarcinae, see the publication by S. T. Lyles entitled "Biology of Microorganisms," pages 195–196, published 1969 by The C. V. Mosby Co., St. Louis, Mo. The above-identified pages of this publication are herein incorporated and made part of this disclosure.

As will be apparent to those skilled in the art in the light of the foregoing disclosure, many modifications, alterations and substitutions are possible in the practice of this invention without departing from the spirit or scope thereof.

We claim:

1. A method of sporulating a microorganism capable of undergoing sporulation which comprises incubating said microorganism in a medium containing filtered cane sugar refinery animal char waste water.

2. A method in accordance with claim 1 wherein said microorganism is *Bacillus popilliae*.

3. A method in accordance with claim 1 wherein said microorganism is *Bacillus lentimorbus*.

4. A method in accordance with claim 1 wherein said microorganism is *Bacillus popilliae* and wherein said microorganism is incubated in said medium at a temperature of about 27°C. for a period of about 24 hours.

5. A method in accordance with claim 4 wherein the resulting produced spores are recovered from the incubation medium by the addition of finely divided talc to the incubation medium and a resulting solids admixture consisting essentially of talc and spores separated and recovered from said incubation medium.

6. A method of producin spores of *Bacillus popilliae* which comprise effecting vegetative growth of *Bacillus popilliae* in a growth medium comprising 1.5% by weight yeast extract, 0.3% weight $K_2$ $HPO_4$, 0.2% by weight glucose and 0.5% by weight triptose, the pH of said growth medium having been adjusted to a value in the range about 7.2-7.3, said growth medium having been sterilized before being employed for the vegetative growth of *Bacillus popilliae* therein, recovering the resulting produced cells of *Bacillus popilliae*, introducing the recovered cells of *Bacillus popilliae* into an incubating medium for effecting sporulation of said cells, said incubating medium comprising filtered cane sugar refinery animal char waste water, incubating the cells in said incubating medium to induce sporulation of said cells and recovering the resulting *Bacillus popilliae* spores.

7. A method in accordance with claim 6 wherein said cane sugar refinery waste water has the composition:

| Component | Range % By Wt. |
|---|---|
| Sucrose | 0.3–2.5 |
| Reducing Sugars | 0.03–0.15 |
| Ash Sulfated | 0.3–0.8 |
| Ash Thermal | 0.15–0.4 |
| Solids (Drying) | 1.1–2.1 |
| ppm Calcium | 500–1500 |
| ppm Magnesium | 60–150 |
| ppm Sodium | 20–90 |
| ppm Potassium | 50–500 |
| ppm Iron | 0.2–9.0 |
| ppm Copper | 0.4–0.9 |
| ppm Zinc | 0.05–0.3 |
| ppm Manganese | 0.1–0.8 |
| ppm Sulfates | 100–1200 |
| ppm Phosphates | 6–40 |
| ppm Chlorides | 1–60. |

8. A method in accordance with claim 6 wherein said cane sugar refinery waste water has the composition:

| Composition | Char Waste Water A % By Wt. |
|---|---|
| Sucrose | 0.60% |
| Reducing Sugars | 0.054% |
| Ash Sulfated | 0.40% |
| Ash Thermal | 0.255% |
| Solids (Drying) | 1.30% |
| ppm Calcium | 792 |
| ppm Magnesium | 93.8 |
| ppm Sodium | 32.5 |
| ppm Potassium | 117 |
| ppm Iron | 1.3 |
| ppm Copper | 0.61 |
| ppm Zinc | 0.18 |
| ppm Manganese | 0.33 |
| ppm Sulfates | 282 |
| ppm Phosphates | 15.96 |
| ppm Chlorides | 2.1. |

9. A method in accordance with claim 6 wherein said cane sugar refinery waste water has the composition:

| Component | Char Waste Water B % By Wt. |
|---|---|
| Sucrose | 1.58% |
| Reducing Sugars | 0.082% |
| Ash Sulfated | 0.45% |
| Ash Thermal | 0.256% |
| Solids (Drying) | 1.58% |
| ppm Calcium | 850 |
| ppm Magnesium | 105 |
| ppm Sodium | 64 |
| ppm Potassium | 247 |
| ppm Iron | 3.92 |
| ppm Copper | 0.57 |
| ppm Zinc | 0.12 |
| ppm Manganese | 0.29 |
| ppm Sulfates | 689 |
| ppm Phosphates | 13 |
| ppm Chlorides | 13.2. |

10. A method in accordance with claim 6 wherein said spores are recovered by the addition of finely divided insoluble, inert solids material to said incubating medium and separating therefrom the resulting solids admixture containing said solids material and said spores.

* * * * *

UNITED STATES PATENT AND TRADEMARK OFFICE
CERTIFICATE OF CORRECTION

PATENT NO. : 3,950,225
DATED : April 13, 1976
INVENTOR(S) : RICHARD DAVID SKOLE & ANTHONY BENNY RIZZUTO It is certified that error appears in the above-identified patent and that said Letters Patent are hereby corrected as shown below:

Column 3, the last sentence should correctly read

-- It has also been reported that a medium deficiency in potassium, phosphates and magnesium prevents most Bacillus from sporulating or reduces........   --

Column 6, Claim 6, first line, "producin" should correctly read -- producing --

Signed and Sealed this

Twenty-fourth Day of August 1976

[SEAL]

Attest:

RUTH C. MASON
Attesting Officer

C. MARSHALL DANN
Commissioner of Patents and Trademarks